(12) United States Patent
Kozawa et al.

(10) Patent No.: US 7,807,846 B2
(45) Date of Patent: Oct. 5, 2010

(54) METHOD FOR PRODUCING SUCCINIMIDE COMPOUND

(75) Inventors: Masami Kozawa, Funabashi (JP); Hideki Musashi, Funabashi (JP)

(73) Assignees: Nissan Chemical Industries, Ltd., Tokyo (JP); DaiNippon Sumitomo Pharma Co., Ltd., Osaka (JP)

( * ) Notice: Subject to any disclaimer, the term of this patent is extended or adjusted under 35 U.S.C. 154(b) by 37 days.

(21) Appl. No.: 12/311,284

(22) PCT Filed: Sep. 26, 2007

(86) PCT No.: PCT/JP2007/068667
§ 371 (c)(1), (2), (4) Date: Mar. 25, 2009

(87) PCT Pub. No.: WO2008/050570
PCT Pub. Date: May 2, 2008

(65) Prior Publication Data
US 2010/0004464 A1    Jan. 7, 2010

(30) Foreign Application Priority Data
Sep. 27, 2006  (JP) ............................. 2006-262249

(51) Int. Cl.
C07D 207/12 (2006.01)
C07D 207/40 (2006.01)
(52) U.S. Cl. ...................... 548/531; 548/546
(58) Field of Classification Search ................ 548/531, 548/546
See application file for complete search history.

(56) References Cited

FOREIGN PATENT DOCUMENTS

| EP | 0 520 320 A2 | 12/1992 |
|---|---|---|
| JP | A-05-186472 | 7/1993 |
| JP | A-06-192222 | 7/1994 |
| WO | WO 95/29909 | 11/1995 |

OTHER PUBLICATIONS

T. Negoro et al., "Novel, Highly Potent Aldose Reductase Inhibitors: (R)-(−)-2-(4-Bromo-2-fluorobenzyl)-1,2,3,4-tetrahydropyrrolo[1,2-a] pyrazine-4-spiro-3'-pyrrolidine-1,2',3,5'-tetrone (AS-3201) and Its Congeners;" J. Med. Chem. 1998, vol. 41, pp. 4118-4129.

F. McMillan et al., "Diethyl N-Benzyl-*dl*-aspartate and Related Compounds," Journal of the American Chemical Society, vol. 70, No. 11, Nov. 1948, pp. 3778-3781.

European Search Report issued in European Patent Application No. EP 07 80 7882.1, mailed on Mar. 11, 2010.

Negoro et al., "Novel, Highly Potent Aldose Reductase Inhibitors: (R)-(−)-2-(4-Bromo-2-fluorobenzyl)-1,2,3,4-tetrahydropyrrolo[1,2-α] pyrazine-4-spiro-3'-pyrrolidine-1,2',3,5'-tetrone (AS-3201) and Its Congeners," *J. Med. Chem*, vol. 41, No. 21, pp. 4118-4129, 1998.

*Primary Examiner*—Kamal A Saeed
*Assistant Examiner*—Kristin Bianchi
(74) *Attorney, Agent, or Firm*—Oliff & Berridge, PLC

(57) ABSTRACT

There is provided a method for producing a succinimide compound. The method for producing a succinimide compound of formula (3) comprises reacting an aminomalonic ester compound of formula (1) with a compound of formula (2) in a solvent in the presence of a base, wherein an alcohol is used as the solvent and an alkali metal alkoxide is used as the base.

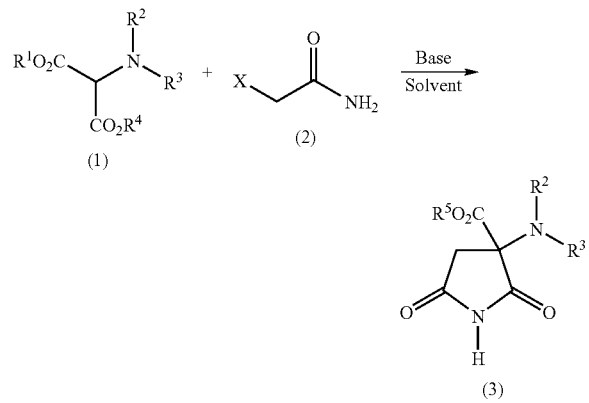

(where $R^1$ and $R^4$ independently represent an alkyl group having 1 to 12 carbon atom(s) which may be a straight chain, branched or cyclic, etc., $R^2$ and $R^3$ independently represent a hydrogen atom, etc., $R^5$ represents an alkyl group having 1 to 12 carbon atom(s) which may be straight chain, branched or cyclic, etc.).

4 Claims, No Drawings

METHOD FOR PRODUCING SUCCINIMIDE COMPOUND

TECHNICAL FIELD

The present invention relates to a method for producing a succinimide compound and more specifically, relates to a method practicable with low cost, safety and a short process and capable of producing a succinimide compound with a higher yield than that of a production method known in a related art. In addition, a compound obtained according to the production method of the present invention is a useful compound utilized as an intermediate raw material for producing pharmaceutical products or the like.

BACKGROUND ART

In the related art, as a method for producing succinimide compounds, known are a method in which a cyano acetic acid ester derivative is alkylated with an α-haloacetic acid ester and thereafter, the resultant alkylated compound is oxidized with hydrogen peroxide or the like and is imidized and a method in which an aminomalonic acid ester derivative is alkylated with an α-haloacetonitrile, thereafter is oxidized with hydrogen peroxide or the like in a similar manner as the above method to imidize it (see Patent Document 1, Patent Document 2 and Non-patent Document 1).

Here, Patent Document 1 describes a method for synthesizing succinimide compounds directly from a reaction of aminomalonic acid derivatives with haloacetamide derivatives whose reaction form is the same reaction form as described in the present specification.

[Patent Document 1]

Japanese Patent Application Publication No. JP-A-6-192222

[Patent Document 2]

Japanese Patent Application Publication No. JP-A-5-186472

[Non-patent Document 1]

J. Med. Chem. (1998), 41, p. 4118-4129

DISCLOSURE OF THE INVENTION

Problems to be Solved by the Invention

However, a method in which a cyanoacetic acid ester derivative is alkylated by an α-haloacetic acid ester and thereafter, the resultant product is oxidized by hydrogen peroxide or the like to imidize it or a method in which an aminomalonic acid ester derivative is alkylated by an α-haloacetonitrile and thereafter, the resultant product is oxidized by hydrogen peroxide or the like to imidize it, is a production method requiring a long process and having a problem in the safety because peroxides are used.

In addition, in a known method for producing a succinimide compound directly from a haloacetamide, the yield of the imide compound which is the objective product is low (36.5%) and many by-products are generated, so that the purification by a column chromatography is necessary and the method is industrially impracticable.

Therefore, a method capable of producing a succinimide compound directly from a haloacetamide with high yield and high purity which is impossible by a related-art method, has been desired.

Means for Solving the Problems

The present inventors have made extensive and intensive studies to achieve the above problems and as a result, a reaction condition capable of obtaining an objective substance with high yield by suppressing a consecutive reaction and a side reaction, has been found.

That is, the present invention provides, according to a first aspect, a method for producing a succinimide compound represented by formula (3):

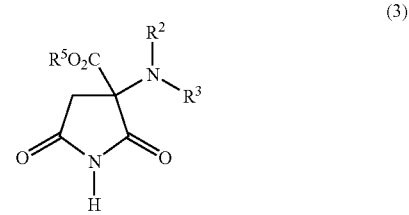

(3)

(where $R^5$ represents an alkyl group having 1 to 12 carbon atom(s) which may be straight chain, branched or cyclic, or an aromatic group having 6 to 12 carbon atoms which may be substituted; and $R^2$ and $R^3$ represent the same as defined in formula (1)), the method includes: reacting an aminomalonic acid ester compound represented by the formula (1):

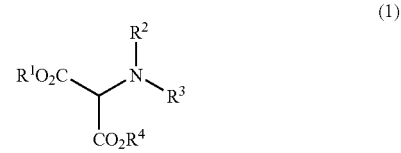

(1)

(where $R^1$ and $R^4$ independently represent an alkyl group having 1 to 12 carbon atom(s) which may be a straight chain, branched or cyclic, or an aromatic group having 6 to 12 carbon atoms which may be substituted; and $R^2$ and $R^3$ independently represent a hydrogen atom, an alkyl group having 1 to 12 carbon atom(s) which may be a straight chain, branched or cyclic, an acyl group having 2 to 6 carbon atoms which may be substituted, an alkoxycarbonyl group having 1 to 6 carbon atom(s) which may be substituted, a benzyl group of which an aromatic ring part may be substituted or a benzyloxycarbonyl group of which an aromatic ring part may be substituted, or $R^2$ and $R^3$ together with a nitrogen atom to which $R^2$ and $R^3$ are bonded form a ring), with a compound represented by formula (2):

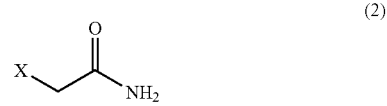

(2)

(where X represents a halogen atom), in a solvent in the presence of a base, in which an alcohol is used as the solvent and an alkali metal alkoxide is used as the base;

according to a second aspect, in the production method according to the first aspect, ethanol is used as the solvent and sodium ethoxide is used as the base; and according to a third aspect in the production method according to the first aspect or the second aspect, the aminomalonic acid ester compound represented by the formula (1) is a compound in which $R^1$ and $R^4$ represent an ethyl group; $R^2$ represents a hydrogen atom; and $R^3$ represents a benzyloxycarbonyl group, and the succinimide compound represented by the formula (3) is a compound represented by formula (4)

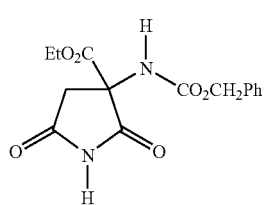

(4)

(where Et represents an ethyl group and Ph represents a phenyl group).

Effects of the Invention

According to the production method of the present invention, a succinimide compound useful as an intermediate raw material for pharmaceutical products or the like can be produced inexpensively, in a short process and safely.

Moreover, according to the production method of the present invention, a succinimide compound can be produced with higher yield than that of a known production method.

BEST MODES FOR CARRYING OUT THE INVENTION

The definition of substituents of the present invention is shown as follows. Here, n—means normal, i—means iso, sec—means secondary and t—means tertiary.

An alkyl group having 1 to 12 carbon atom(s) which may be straight chain, branched or cyclic in the present specification represents a strait chain, branched or cyclic hydrocarbon group containing 1 to 12 carbon atom(s) and specific examples thereof include a methyl group, an ethyl group, an n-propyl group, an i-propyl group, a cyclopropyl group, an n-butyl group, an i-butyl group, a sec-butyl group, a t-butyl group, a cyclobutyl group, an n-pentyl group, a cyclopentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, n-hexyl group, a cyclohexyl group, a 1-methylpentyl group, a 2-methylpentyl group, a 1,1-dimethylbutyl group, a 1,3-dimethylbutyl group, a heptyl group, a cycloheptyl group, an octyl group, a cyclooctyl group, a nonyl group, a decyl group, an undecyl group, a dodecyl group and an adamantyl group.

Examples of the aromatic group having 6 to 12 carbon atoms which may be substituted include a phenyl group and a naphthyl group which may be substituted with one or more substituent(s) the same as or different from each other which is (are) selected from a halogen atom, an alkyl group having 1 to 12 carbon atom(s), a cyano group, a nitro group, an alkylcarbonyl group having 1 to 12 carbon atom(s), an alky-loxy group having 1 to 12 carbon atom(s), di(alkyl having 1 to 12 carbon atom(s)) amino group, and the like.

Examples of the acyl group having 2 to 6 carbon atoms which may be substituted include a methylcarbonyl group, an ethylcarbonyl group, an n-propylcarbonyl group, an i-propylcarbonyl group, an n-butylcarbonyl group, an i-butylcarbonyl group, a sec-butylcarbonyl group, a t-butylcarbonyl group and an n-pentylcarbonyl group which may be substituted with one or more substituent(s) the same as or different from each other which is/are selected from a fluorine atom, a chlorine atom, a bromine atom, an iodine atom, a nitro group, a cyano group, and the like.

Examples of the alkoxycarbonyl group having 1 to 6 carbon atom(s) which may be substituted include a methoxycarbonyl group, an ethoxycarbonyl group, an n-propyloxycarbonyl group, an i-propyloxycarbonyl group, an n-butyloxycarbonyl group, an i-butyloxycarbonyl group, a sec-butyloxycarbonyl group, a t-butyloxycarbonyl group, an n-pentyloxycarbonyl group and an n-hexyloxycarbonyl group which may be substituted with one or more substituent(s) the same as or different from each other which is/are selected from a fluorine atom, a chlorine atom, a bromine atom, an iodine atom, a nitro group, a cyano group and the like.

Examples of the benzyl group of which an aromatic ring part may be substituted represent a benzyl group of which an aromatic part may be substituted with one or more substituent(s) the same as or different from each other which is/are selected from a halogen atom, an alkyl group having 1 to 12 carbon atom(s), a cyano group, a nitro group, an alkylcarbonyl group having 1 to 12 carbon atom(s), an alkyloxy group having 1 to 12 carbon atom(s), di(alkyl having 1 to 12 carbon atom(s)) amino group, and the like.

Examples of the benzyloxycarbonyl group of which an aromatic ring part may be substituted represent a benzyloxycarbonyl group of which an aromatic part may be substituted with one or more substituent(s) the same as or different from each other which is/are selected from a halogen atom, an alkyl group having 1 to 12 carbon atom(s), a cyano group, a nitro group, an alkylcarbonyl group having 1 to 12 carbon atom(s), an alkyloxy group having 1 to 12 carbon atom(s), di(alkyl having 1 to 12 carbon atom(s)) amino group, and the like.

"$R^2$ and $R^3$ together with a nitrogen atom to which $R^2$ and $R^3$ are bonded form a ring" means that $R^2$ and $R^3$ together with a nitrogen atom to which $R^2$ and $R^3$ are bonded form a piperidine ring, a pyrrolidine ring, a succinimide ring, a maleimide ring, or the like.

Next, examples of the preferred substituent are as follows.

Examples of preferred $R^1$ and $R^4$ independently include a methyl group, an ethyl group, an n-propyl group, an i-propyl group, an n-butyl group, an i-butyl group, a sec-butyl group, a t-butyl group and a benzyl group.

Examples of preferred $R^2$ include a hydrogen atom, a methyl group, an ethyl group and an n-propyl group.

Examples of preferred $R^3$ include a benzyl group, a benzyloxycarbonyl group, an acetyl group and a t-butyloxycarbonyl group.

Examples of preferred X include a chlorine atom, a bromine atom and an iodine atom.

Hereinafter, the present invention will be described in more detail.

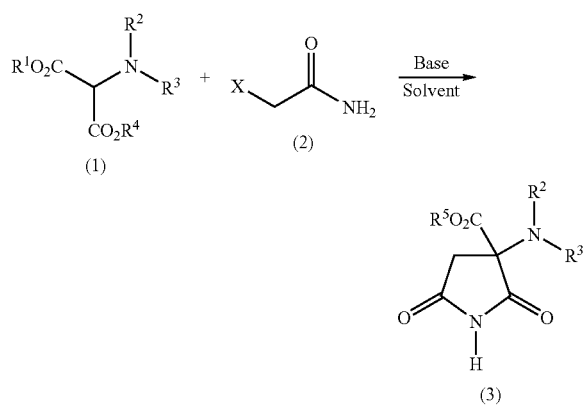

That is, an aminomalonic acid derivative represented by the formula (1) and an α-haloacetamide represented by the formula (2) are mixed in a solvent and by adding a base to the resultant mixture, α-position of the aminomalonic acid derivative is alkylated. Then, a cyclization is caused immediately in the reaction system and a succinimide compound represented by the formula (3) can be produced. $R^5$ in the formula (3) is any of $R^1$, $R^4$ in the formula (1) and a group resulted from a transesterification with an alcohol in the reaction system accordingly. Here, when $R^1$ and $R^4$ are substituents different from each other, a mixture may be provided, so that in terms of avoiding such a mixture, $R^1$ and $R^4$ are preferably the same substituent as each other.

As the α-haloacetamide, for example α-chloroacetamide, α-bromoacetamide and α-iodoacetamide can be used, and preferably α-bromoacetamide and α-iodoacetamide are used, more preferably α-iodoacetamide is used. In this case, α-iodoacetamide prepared by a halogen exchange in the reaction system may also be used.

Examples of the base to be used include alkali metal alkoxides such as sodium ethoxide, potassium ethoxide, sodium methoxide, potassium methoxide, potassium t-butoxide and sodium pentoxide and preferred examples thereof include sodium ethoxide and sodium methoxide. In the selection of the base, when a transesterification is not desired, for example, sodium ethoxide is desirably selected for ethyl ester.

Examples of the solvent to be used include alcohols such as ethanol, methanol, n-propanol and i-propanol and preferred examples thereof include ethanol and methanol. In the selection of the solvent, when a transesterification is not desired, for example, ethanol is desirably selected for ethyl ester.

In addition, the solvent may be a mixture with another solvent (such as toluene, hexane and ethyl acetate) so long as the solvent does not participate in the reaction.

The amount used of the base is 1 to 10 equivalent(s), preferably 1.5 to 3 equivalents, more preferably 1.8 to 2.5 equivalents relative to the amount of an aminomalonic acid ester compound represented by the formula (1).

The amount used of the solvent can be 1 to 200 times, preferably 3 to 20 times the mass of an aminomalonic acid ester compound represented by the formula (1).

The amount used of the compound represented by the formula (2) α-haloacetamide) is 0.5 to 10 equivalents, preferably 1 to 2 equivalent(s) relative to the amount of the aminomalonic acid ester compound represented by the formula (1).

The reaction temperature is usually within a temperature range of from −20° C. to the boiling point of a solvent used, preferably within a temperature range of from −10° C. to 20° C., more preferably within a temperature range of from −10° C. to 10° C.

The order of adding the reagents is not limited to the above-described order.

Here, when a similar reaction is performed under a condition other than the combination of a base and a solvent defined by the present invention, a consecutive reaction is difficult to be suppressed and a large amount of a consecutive reaction product represented by the formula (5):

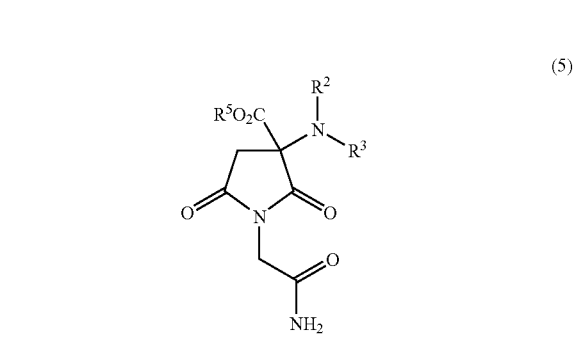

is produced (in many cases, in a larger amount than that of the objective product represented by the formula (3)).

However, under the reaction condition of the present invention, the consecutive reaction can be suppressed at 10% or less and under the optimal condition, the consecutive reaction can be suppressed at 2% or less, so that a succinimide compound represented by the formula (3) which is an objective product can be obtained with high selectivity and high yield.

The succinimide compound represented by the formula (3) obtained by the reaction can be obtained, for example, after the completion of the reaction, by quenching the reaction with an acid, by extracting with an appropriate solvent and by washing with water, and if necessary, can be purified by a recrystallization, a distillation, a silica-gel chromatography, and the like.

EXAMPLES

Hereinafter, the present invention is described specifically referring to examples, however, which should not be construed as limiting the scope of the present invention.

Here, the quantitative yield of the succinimide compound represented by the formula (4) was determined by performing a quantitative analysis using a reversed phase high performance liquid chromatography and using p-t-butylphenol as an internal standard substance.

| | |
|---|---|
| Column: | XBridge C18 (manufactured by Waters Corporation) |
| Eluent: | water/acetonitrile/acetic acid = 58/42/0.1 (in volume ratio) |
| Oven temperature: | 40° C. |
| Detection method: | UV 210 nm |

Example 1

Production of 2-benzyloxycarbonylamino-2-ethoxycarbonyl succinimide

To 45 g of ethanol, 10.4 g (56.2 mmol) of α-iodoacetamide was added and 21.4 g (48.2 mmol) of 70% toluene solution of diethyl 2-benzyloxycarbonylaminomalonate was added, followed by cooling the resultant mixture to 0° C. Thereto, 33.0 g (97.0 mmol) of 20% ethanol solution of sodium ethoxide was dropped for 1 hour while maintaining the temperature at 0° C. The reaction mixture was stirred at 0° C. for 3 hours and the reaction liquid was quantitated to find that 2-benzyloxycarbonylamino-2-ethoxycarbonyl succinimide was produced in an amount of 13.7 g (yield: 89%).

Example 2

Production of 2-benzyloxycarbonylamino-2-ethoxycarbonyl succinimide

To 123 kg of ethanol, 25.0 kg (167 mol) of sodium iodide and 14.2 kg (152 mol) of α-chloroacetamide were added and the resultant mixture was heated to 77° C. and was stirred for 3 hours. To the resultant suspension, 58.2 kg (130 mol) of 69% toluene solution of diethyl 2-benzyloxycarbonylaminomalonate was added, followed by cooling the resultant mixture to 0° C. Thereto, 89.1 kg (262 mol) of 20% ethanol solution of sodium ethoxide was dropped for 3 hours while maintaining the temperature at 0° C. After the reaction mixture was stirred for 3 hours at 0° C., the reaction was quenched by adding 7.9 kg of acetic acid and 15.1 kg of 85% phosphoric acid to the reaction mixture and the solvent was distilled off under reduced pressure. To the reaction mixture, 200 kg of toluene and 80 kg of water were added and the phase separation of the reaction mixture was performed. After the organic phase was washed with water 3 times, it was quantitatively analyzed and the yield of 2-benzyloxycarbonylamino-2-ethoxycarbonyl succinimide was found to be 87.5%. This solution was concentrated and then was recrystallized with toluene and ethanol to thereby obtaining 30 kg (yield: 72%) of 2-benzyloxycarbonylamino-2-ethoxycarbonyl succinimide as a white crystal.

Here, diethyl 2-benzyloxycarbonylaminomalonate used in the present examples was synthesized according to a common method from diethyl 2-aminomalonate hydrochloride and benzyloxycarbonyl chloride using sodium carbonate as the base.

INDUSTRIAL APPLICABILITY

The production method of the present invention is to provide a high-efficiency production method of a succinimide compound useful as an intermediate raw material for pharmaceutical products or the like.

The invention claimed is:

1. A method for producing a succinimide compound represented by the formula (3):

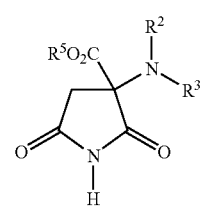

(where $R^5$ represents an alkyl group having 1 to 12 carbon atom(s) which may be straight chain, branched or cyclic, or an aromatic group having 6 to 12 carbon atoms which may be substituted; and $R^2$ and $R^3$ represent the same as defined in formula (1)), the method comprising:

reacting an aminomalonic acid ester compound represented by the formula (1):

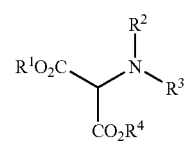

(where $R^1$ and $R^4$ independently represent an alkyl group having 1 to 12 carbon atom(s) which may be a straight chain, branched or cyclic, or an aromatic group having 6 to 12 carbon atoms which may be substituted; and $R^2$ and $R^3$ independently represent a hydrogen atom, an alkyl group having 1 to 12 carbon atom(s) which may be a straight chain, branched or cyclic, an acyl group having 2 to 6 carbon atoms which may be substituted, an alkoxycarbonyl group having 1 to 6 carbon atom(s) which may be substituted, a benzyl group of which an aromatic ring part may be substituted or a benzyloxycarbonyl group of which an aromatic ring part may be substituted, or $R^2$ and $R^3$ together with a nitrogen atom to which $R^2$ and $R^3$ are bonded form a ring), with a compound represented by formula (2):

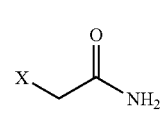

(where X represents a halogen atom),
in a solvent in the presence of a base, wherein an alcohol is used as the solvent and an alkali metal alkoxide is used as the base.

2. The production method according to claim 1, wherein ethanol is used as the solvent and sodium ethoxide is used as the base.

3. The production method according to claim 1, wherein the aminomalonic acid ester compound represented by the formula (1) is a compound in which $R^1$ and $R^4$ represent an ethyl group; $R^2$ represents a hydrogen atom; and $R^3$ represents a benzyloxycarbonyl group, and the succinimide compound represented by the formula (3) is a compound represented by formula (4)

(4)

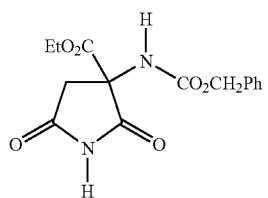

(where Et represents an ethyl group and Ph represents a phenyl group).

4. The production method according to claim 2, wherein the aminomalonic acid ester compound represented by the formula (1) is a compound in which $R^1$ and $R^4$ represent an ethyl group; $R^2$ represents a hydrogen atom; and $R^3$ represents a benzyloxycarbonyl group, and the succinimide compound represented by the formula (3) is a compound represented by formula (4)

(4)

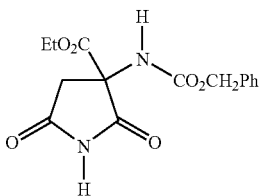

(where Et represents an ethyl group and Ph represents a phenyl group).

* * * * *